United States Patent
Tsujimoto (10) Patent No.: US 10,330,907 B2
(45) Date of Patent: Jun. 25, 2019

(54) CELL IMAGING CONTROL DEVICE, METHOD, AND PROGRAM

(71) Applicant: FUJIFILM Corporation, Tokyo (JP)

(72) Inventor: Takayuki Tsujimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 174 days.

(21) Appl. No.: 15/271,634

(22) Filed: Sep. 21, 2016

(65) Prior Publication Data

US 2017/0010455 A1 Jan. 12, 2017

Related U.S. Application Data

(63) Continuation of application No. PCT/JP2015/054412, filed on Feb. 18, 2015.

(30) Foreign Application Priority Data

Mar. 31, 2014 (JP) ................. 2014-071378

(51) Int. Cl.
G02B 21/24 (2006.01)
G02B 7/28 (2006.01)
(Continued)

(52) U.S. Cl.
CPC ......... *G02B 21/244* (2013.01); *G01N 33/483* (2013.01); *G02B 7/28* (2013.01);
(Continued)

(58) Field of Classification Search
CPC ...... G02B 21/244; G02B 7/28; G01N 33/483; G01N 7/36; G01N 21/36; G01N 21/365;
(Continued)

(56) References Cited

U.S. PATENT DOCUMENTS 8,873,027 B2 * 10/2014 Sugiyama .......... G01N 15/1475
356/28.5
9,025,881 B2 * 5/2015 Dauwels ............... G06T 7/0002
359/11
(Continued)

FOREIGN PATENT DOCUMENTS

JP 6-138119 A 5/1994
JP 10-502466 A 3/1998
(Continued)

OTHER PUBLICATIONS

International Search Report for PCT/JP2015/054412 (PCT/ISA/210) dated May 19, 2015.
(Continued)

*Primary Examiner* — Jamie J Atala
*Assistant Examiner* — James T Boylan
(74) *Attorney, Agent, or Firm* — Birch, Stewart, Kolasch & Birch, LLP (57) ABSTRACT

The cell imaging control device includes a cell detection unit 22 that acquires a cell image by imaging transmitted light or reflected light of undyed cells and detects the cells or structures in the cells in the cell image and an autofocus control unit 24 that calculates an autofocus evaluation value based on image information of the cells or the structures detected by the cell detection unit 22 and outputs an autofocus control signal based on the autofocus evaluation value to an imaging device for capturing the cell image, which is an imaging device having an autofocus function.

14 Claims, 6 Drawing Sheets

(51) Int. Cl.
  *G02B 7/36* (2006.01)
  *G02B 21/36* (2006.01)
  *H04N 5/232* (2006.01)
  *H04N 5/225* (2006.01)
  *G01N 33/483* (2006.01)
  *G06T 7/00* (2017.01)

(52) U.S. Cl.
  CPC .............. *G02B 7/36* (2013.01); *G02B 21/36* (2013.01); *G02B 21/365* (2013.01); *G06T 7/0012* (2013.01); *H04N 5/2256* (2013.01); *H04N 5/23212* (2013.01); *G06T 2207/10056* (2013.01); *G06T 2207/30024* (2013.01)

(58) Field of Classification Search
  CPC ......... G06T 7/0012; G06T 2207/10056; G06T 2207/30024; H04N 5/2256; H04N 5/23212
  USPC .............................................. 348/79, 208.12
  See application file for complete search history.

(56) References Cited

U.S. PATENT DOCUMENTS

| | | | |
|---|---|---|---|
| 9,315,847 B2* | 4/2016 | Charlot | ................. G06T 7/0016 |
| 9,349,762 B2* | 5/2016 | Cho | ................. H01L 27/14601 |
| 2007/0052837 A1 | 3/2007 | Onozawa | |
| 2008/0002868 A1 | 1/2008 | Ando et al. | |
| 2010/0182417 A1 | 7/2010 | Takagi et al. | |
| 2010/0232674 A1 | 9/2010 | Amakawa et al. | |
| 2013/0016885 A1 | 1/2013 | Tsujimoto | |
| 2015/0098005 A1* | 4/2015 | Tsai | ................... H04N 5/23212 |
| | | | 348/336 |

FOREIGN PATENT DOCUMENTS

| | | |
|---|---|---|
| JP | 2008-5768 A | 1/2008 |
| JP | 2008-46305 A | 2/2008 |
| JP | 2008-116526 A | 5/2008 |
| JP | 2010-216920 A | 9/2010 |
| JP | 4797522 B2 | 10/2011 |
| JP | 2013-20212 A | 1/2013 |
| WO | WO 96/01438 A1 | 1/1996 |

OTHER PUBLICATIONS

Written Opinion of the International Searching Authority for PCT/JP2015/054412 (PCT/ISA/237) dated May 19, 2015.
Japanese Notification of Reasons for Refusal dated Apr. 4, 2017, for corresponding Japanese Application No. 2014-071378, including English translation.

* cited by examiner

CELL IMAGING CONTROL DEVICE, METHOD, AND PROGRAM

CROSS-REFERENCE TO RELATED APPLICATIONS

This application is a Continuation of PCT International Application No. PCT/JP2015/054412 filed on Feb. 18, 2015, which claims priority under 35 U.S. § 119(a) to Patent Application No. 2014-071378 filed in Japan on Mar. 31, 2014, all of which are hereby expressly incorporated by reference into the present application.

BACKGROUND OF THE INVENTION

1. Field of the Invention

The present invention relates to a cell imaging control device, method, and non-transitory computer readable recording medium storing a program for performing autofocus control in an imaging device having an autofocus function that is an imaging device for imaging undyed cells.

2. Description of the Related Art

Conventionally, a method of temporally imaging pluripotent stem cells, such as ES cells, iPS cells, and STAP cells, or differentiation-induced cells and determining the quality of the culture state of the cells by checking a temporal variation in the image has been proposed.

In addition, as a device for imaging cells as described above, a microscope is used. However, when capturing an image of cells with a microscope, so-called autofocus control is performed so that the image of cells is captured in a state of an optimal focus position.

As a general autofocus method, JP4797522B, JP2008-116526A, JP1994-138119A (JP-H06-138119A), and JP2008-5768A have proposed a method of acquiring a blur-free image by calculating an AF evaluation value from the contrast of an entire acquired image and selecting a focus position where the AF evaluation value is maximized.

JP2013-20212A has proposed a method of acquiring a blur-free cell image by dividing a cell image, which is obtained by imaging cells, into regions, calculating an AF evaluation value based on the contrast for each of the regions, selecting a focus position where the AF evaluation value is maximized, and combining images of the respective regions at the selected focus positions.

JP2010-216920A has proposed focusing for emphasizing the contour portion of cells in order to observe individual cells more clearly.

SUMMARY OF THE INVENTION

However, in the case of acquiring a microscopic image of cells by performing control for a focus position where the contrast is the maximum as in the methods disclosed in JP4797522B, JP2008-116526A, JP1994-138119A (JP-H06-138119A), JP2008-5768A, and JP2013-20212A, for example, in a case where floating matter, such as dead cells or dust, is floating on a culture medium (culture fluid), control may be performed such that an unintended focus position is obtained due to the influence of such floating matter. In addition, there may be cases where the search range of the focus position is not appropriate due to the height of cells themselves. Also in this case, there is a case where control is performed such that an unintended focus position is obtained.

Even if imaging for emphasizing the contours of cells is performed as in the method disclosed in JP2010-216920A, control to obtain the focus position where a structure, such as a nucleus or a nucleolus, in each cell can be clearly observed is not necessarily realized.

In order to prevent dead cells or dust from controlling the focus position as described above, JP2008-46305A has proposed excluding a range of high-brightness pixels showing dead cells or dust from the focus search range based on the density histogram of the cell image and searching for a focus position only in the brightness range of an image of living cells.

However, the method disclosed in JP2008-46305A is a focus control method when capturing a fluorescence image of cells dyed with fluorescent material. Basically, the method disclosed in JP2008-46305A is an autofocus control based on the contrast of the entire cell image similar to the methods disclosed in JP4797522B, JP2008-116526A, JP1994-138119A (JP-H06-138119A), JP2008-5768A, and JP2013-20212A.

Accordingly, this is an applicable method when capturing a high-contrast image, such as a fluorescence image. However, for example, in a case where an imaging target is not a fluorescence image but a phase image captured by a phase contrast microscope, the contrast of the phase image is not as high as in a fluorescence image. For this reason, in the autofocus control method based on the contrast of the entire cell image as in the method disclosed in JP2008-46305A, there is a possibility that the autofocus control cannot be appropriately performed.

In addition, in a case where a cell image is captured under control to obtain an unintended focus position, a cell image that is not suitable for the determination of the quality of cells is captured.

In view of the aforementioned problems, it is an object of the present invention to provide a cell imaging control device, method, and non-transitory computer readable recording medium storing a program capable of capturing a cell image, in which cells to be observed are in focus, without being influenced by floating matter, such as dead cells or dust, the height of cells themselves, and the like.

A cell imaging control device of the present invention comprises: a cell detection unit that acquires a cell image by imaging transmitted light or reflected light of undyed cells by emission of light to the cells and detects the cells or structures in the cells in the cell image; and an autofocus control unit that calculates an autofocus evaluation value based on image information of the cells or the structures detected by the cell detection unit and outputs an autofocus control signal based on the autofocus evaluation value to an imaging device that captures the cell image.

In the cell imaging control device of the present invention described above, a contrast information acquisition unit that acquires contrast information of the cell image can be further provided, and the autofocus control unit can calculate an autofocus evaluation value based on image information of the cells or the structures and an autofocus evaluation value based on the contrast information for the cell image captured by the imaging device using autofocus control based on the autofocus control signal. At this time, in a case where there is a focus position where the autofocus evaluation value based on the contrast information is a maximum and the autofocus evaluation value based on the image information of the cells or the structures is not a maximum, the autofocus control unit can output a control signal to return a focus position to an origin position at the start of autofocus control to the imaging device.

In addition, after returning the focus position to the origin position, the autofocus control unit can perform the autofocus control in a range on the origin position side of a focus position where the autofocus evaluation value based on the contrast information is a maximum.

The origin position can be set at a position of a bottom surface of a container on which the cells are cultured or a position of an installation surface on which the cells are placed.

The autofocus control unit can acquire the number of cells or structures or areas of the cells or the structures based on image information of the cells or the structures, and can calculate the autofocus evaluation value based on the number or the areas.

The autofocus control unit can change a movable range of a focus position.

The autofocus control unit can change the movable range of the focus position based on information regarding sizes of the cells or the structures.

As the structures, it is possible to use nucleoli or nuclei of the cells.

In addition, as the cells, it is possible to use stem cells, cells sampled during efficacy testing, or cells sampled during biopsy.

A cell imaging control method of the present invention includes: acquiring a cell image by imaging transmitted light or reflected light of undyed cells by emission of light to the cells and detecting the cells or structures in the cells in the cell image; and calculating an autofocus evaluation value based on image information of the detected cells or structures and outputting an autofocus control signal based on the autofocus evaluation value to an imaging device that captures the cell image.

Non-transitory computer readable recording medium storing a cell imaging control program of the present invention causes a computer to function as: a cell detection unit that acquires a cell image by imaging transmitted light or reflected light of undyed cells by emission of light to the cells and detects the cells or structures in the cells in the cell image; and an autofocus control unit that calculates an autofocus evaluation value based on image information of the cells or the structures detected by the cell detection unit and outputs an autofocus control signal based on the autofocus evaluation value to an imaging device that captures the cell image.

According to the cell imaging control device, method, and non-transitory computer readable recording medium storing a program of the present invention, a cell image is acquired by imaging transmitted light or reflected light of undyed cells, cells or structures in cells in the cell image are detected, an autofocus evaluation value is calculated based on the image information of the detected cells or structures, and an autofocus control signal based on the autofocus evaluation value is output to the imaging device. Therefore, it is possible to perform focus control with a focus on cells or structures in cells. Therefore, it is possible to capture a cell image, in which cells to be observed are in focus, without being influenced by floating matter, such as dead cells or dust, the height of cells themselves, and the like.

In addition, since this makes it possible to observe microscopic structures in cells more clearly, it is possible to improve the accuracy of the determination of the quality of cells.

DESCRIPTION OF THE PREFERRED EMBODIMENTS

Figure 1:
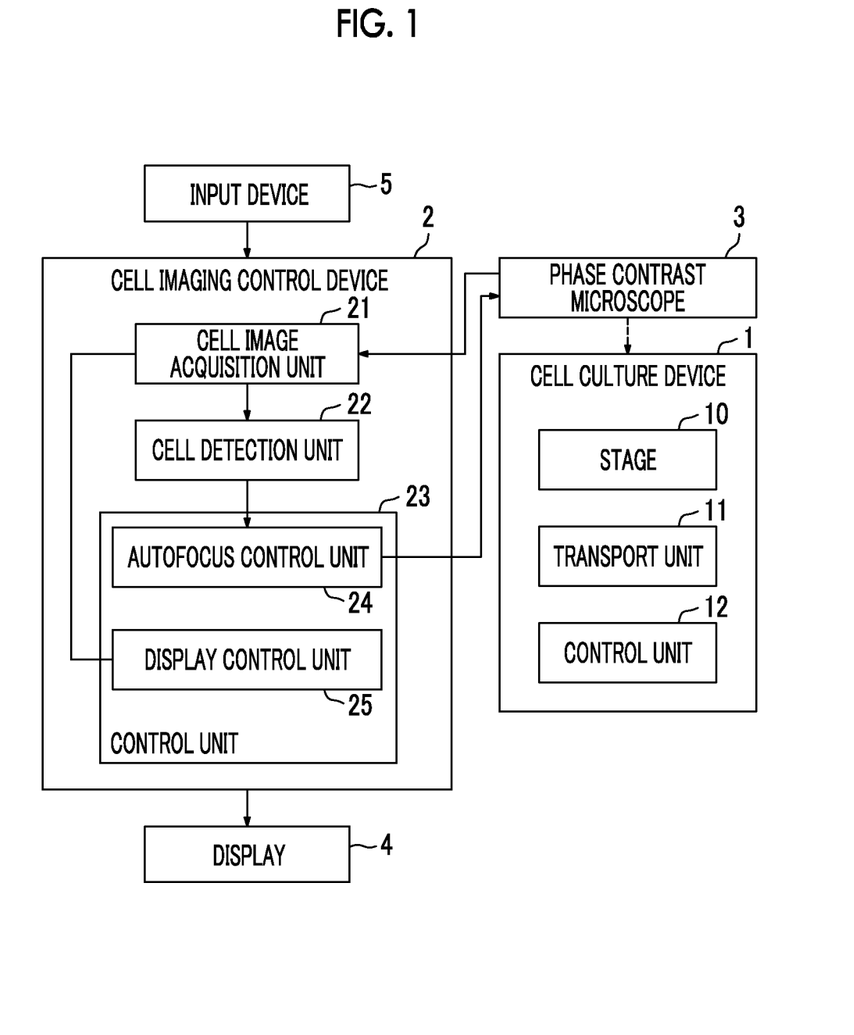
FIG. 1 is a diagram showing the schematic configuration of a cell culture observation system using an embodiment of a cell imaging control device of the present invention.

Hereinafter, a cell culture observation system using an embodiment of a cell imaging control device, method, and non-transitory computer readable recording medium storing a program of the present invention will be described in detail with reference to the diagrams. FIG. 1 is a block diagram showing the schematic configuration of a cell culture observation system.

As shown in FIG. 1, the cell culture observation system includes a cell culture device 1, a cell imaging control device 2, a phase contrast microscope 3, a display 4, and an input device 5.

The cell culture device 1 is a device for culturing cells. As cells to be cultured, for example, there are stem cells such as iPS cells, ES cells, and STAP cells, cells of nerves, skin, and liver that are differentiation-induced from stem cells, and cancer cells. In addition, cells to be cultured may be cells sampled during efficacy testing, or may be cells sampled during the biopsy. In the cell culture device 1, a plurality of culture vessels are housed in which cells to be cultured are seeded on a culture medium. The cell culture device 1 includes a stage 10, a transport unit 11, and a control unit 12.

On the stage 10, a culture vessel to be imaged by the cell imaging control device 2 is placed. As culture vessels, there are a dish, a plate, a flask, and the like. The transport unit 11 selects a culture vessel to be imaged from a plurality of culture vessels housed in a predetermined position in the cell culture device 1, and transports the selected culture vessel to the stage 10.

The control unit 12 controls the entire cell culture device 1. The control unit 12 controls not only the operation of the stage 10 or the transport unit 11 described above but also environmental conditions, such as the temperature, humidity, and $CO_2$ concentration in the cell culture device 1. As the configuration for adjusting the temperature, humidity, and $CO_2$ concentration, it is possible to use a known configuration.

The phase contrast microscope 3 corresponds to an imaging device, and captures phase images of cells within the culture vessel placed on the stage 10. In particular, the phase contrast microscope 3 of the present embodiment captures a phase image of undyed cells. In addition, the phase contrast microscope 3 of the present embodiment has an autofocus function of changing the focus position automatically, and changes a focus position based on an autofocus control signal output from an autofocus control unit 24 to be described later.

Figure 2:
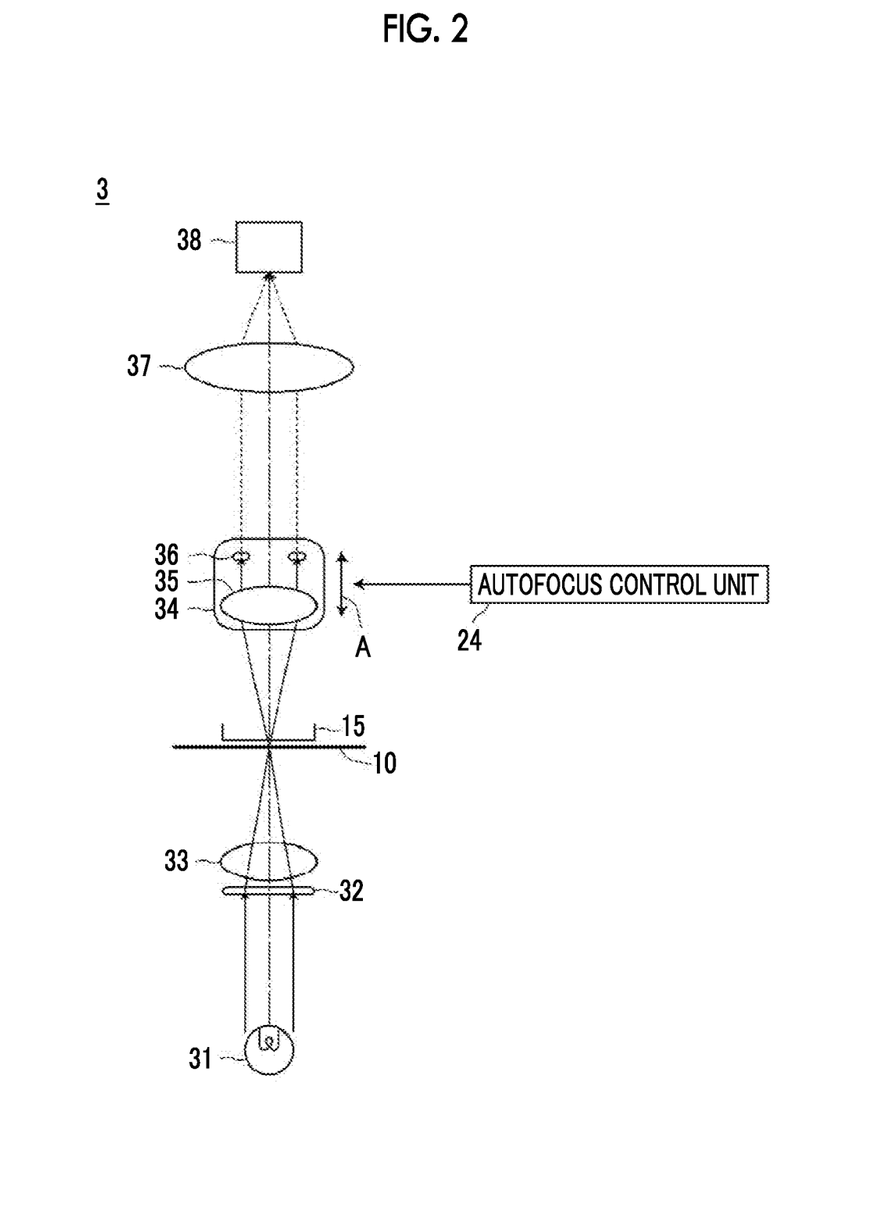
FIG. 2 is a diagram showing the schematic configuration of a phase contrast microscope having an autofocus function.

FIG. 2 is a diagram showing the schematic configuration of the phase contrast microscope 3. As shown in FIG. 2, the phase contrast microscope 3 includes: a white light source 31 which emits white light; a slit plate 32 which has a ring-shaped slit, on which the white light emitted from the white light source 31 is incident, and which emits ring-shaped illumination light; and an objective lens 33 on which the ring-shaped illumination light emitted from the slit plate 32 is incident and which emits the incident ring-shaped illumination light to cells in a culture vessel 15 placed on the stage 10.

In addition, a phase difference lens 34, an imaging lens 37, and an imaging element 38 are provided on the opposite side to the white light source 31 with respect to the stage 10.

The phase difference lens 34 includes an objective lens 35 and a phase plate 36. The phase plate 36 is configured by forming a phase ring on a transparent plate that is transparent for the wavelength of the ring-shaped illumination light. In addition, the size of the slit of the slit plate 32 described above and the phase ring are in the conjugate relationship.

The phase ring is obtained by forming a phase film, which shifts the phase of incident light by ¼ wavelength, and a dimming filter, which is for dimming the incident light, in a ring shape. Direct light incident on the phase difference lens 34 is condensed by the objective lens 35, and is transmitted through the phase ring. As a result, the phase of the direct light is shifted by ¼ wavelength, and the brightness is weakened. On the other hand, most of the diffracted light diffracted by the cells in the culture vessel 15 passes through the transparent plate of the phase plate, and the phase and the brightness are not changed.

The phase difference lens 34 is moved in the arrow A direction shown in FIG. 2 by a driving mechanism (not shown). Since the phase difference lens 34 is moved in this manner, the focus position is changed. The driving mechanism moves the phase difference lens 34 based on the autofocus control signal output from the autofocus control unit 24.

Direct light and diffracted light that are transmitted through the phase difference lens 34 are incident on the imaging lens 37, and an image of these light beams is formed on the imaging element 38. The imaging element 38 captures a phase image of cells by performing photoelectric conversion of the image formed by the imaging lens 37. As the imaging element 38, a charge-coupled device (CCD) image sensor, a complementary metal-oxide semiconductor (CMOS) image sensor, or the like can be used.

Although the phase contrast microscope 3 is used as an imaging device in the present embodiment, other microscopes having an autofocus function of imaging transmitted light or reflected light of cells may be used. For example, a differential interference microscope, a bright field microscope, a dark field microscope, and the like may be used.

Referring back to FIG. 1, the cell imaging control device 2 includes a cell image acquisition unit 21, a cell detection unit 22, and a control unit 23. In addition, the control unit 23 includes the autofocus control unit 24 and a display control unit 25.

The cell imaging control device 2 is formed by installing an embodiment of a cell imaging control program of the present invention in a computer. The cell imaging control device 2 includes a central processing unit, a semiconductor memory, a hard disk, and the like, and an embodiment of the cell imaging control program is installed in the hard disk. When the program is executed by the central processing unit in the control unit 23, the cell image acquisition unit 21, the cell detection unit 22, the autofocus control unit 24, and the display control unit 25 shown in FIG. 1 operate.

The cell imaging control program is stored in a recording medium, such as a DVD or a CD-ROM, a server computer accessible from the outside connected to a network, and the like, and is downloaded and installed in a computer by being read from the recording medium or the server computer described above in response to the request of the user.

The cell image acquisition unit 21 acquires a cell image captured during the autofocus control in the phase contrast microscope 3, and acquires a cell image with the adjusted focus position.

The cell image acquired by the cell image acquisition unit 21 during the autofocus control is input to the cell detection unit 22, and the cell detection unit 22 detects cells or structures in cells in the input cell image.

As a cell detection method, for example, it is preferable to detect the edges of individual cells by performing filtering processing after converting a cell image to a binary image and detect the cells by performing pattern matching for the edges. At the time of pattern matching, it is desirable to perform pattern recognition using machine learning. However, it is possible to use various known methods without being limited to such a method.

Structures in cells are those included in individual cells. For example, the structures in cells are nuclei, nucleoli, or the like. As a method of detecting the nucleus or the nucleolus, it is preferable to detect the nucleus or the nucleolus by edge detection and pattern matching in the same manner as in the case of cells. For the nucleolus, since the nucleolus becomes an image blacker than the surrounding region, the nucleolus may be detected from the brightness, luminance, or the like. Also for the nucleus or the nucleolus, it is possible to use various known methods without being limited to such a method.

The control unit 23 controls the entire cell imaging control device 2. The autofocus control unit 24 in the control unit 23 performs autofocus control of the phase contrast microscope 3. The display control unit 25 displays the cell image captured by the phase contrast microscope 3 on the display 4.

The autofocus control unit 24 performs autofocus control based on the image information of cells or structures in the cell image detected by the cell detection unit 22. Specifically, the autofocus control unit 24 of the present embodiment counts the number of nucleoli in the cell image, calculates that number as an autofocus evaluation value, and performs autofocus control based on the autofocus evaluation value.

Figure 3:
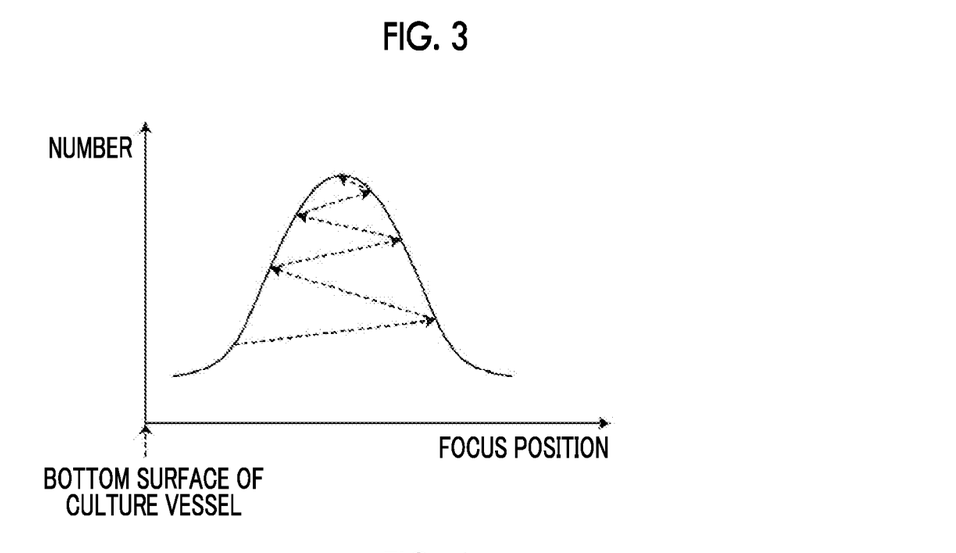
FIG. 3 is a diagram illustrating the algorithm of autofocus control.
Figure 4:
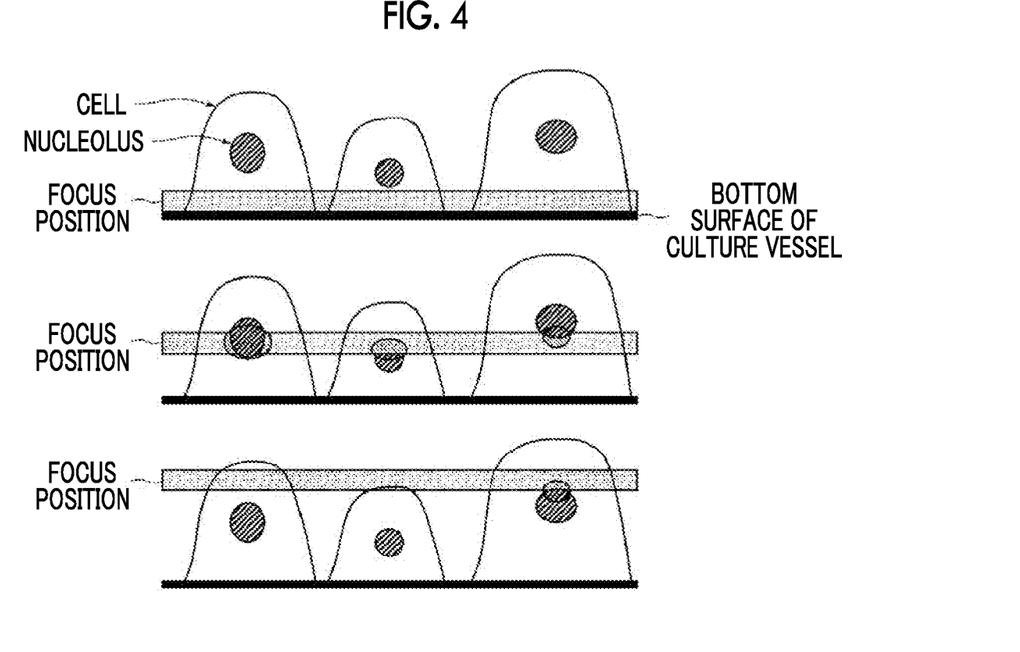
FIG. 4 is an image diagram showing the movement of a focus position by autofocus control.

FIG. 3 is a diagram illustrating the algorithm of the autofocus control of the autofocus control unit 24 of the present embodiment. FIG. 4 is an image diagram showing the movement of the focus position by the autofocus control. The following explanation will be given with reference to FIGS. 3 and 4.

First, the autofocus control unit 24 sets a position of the bottom surface of the culture vessel 15 as an origin position of the focus position, and starts the autofocus control from the origin position. As a method of setting the origin position on the bottom surface of the culture vessel 15, the bottom surface of the culture vessel 15 may be automatically detected using an image captured by the phase contrast microscope 3 or may be set manually, or the origin position may be set in advance by the autofocus control unit 24.

As a method of detecting the bottom surface of the culture vessel 15, for example, a mark or the like may be provided, and the bottom surface may be detected by detecting the mark. Alternatively, a light source may be separately provided, the bottom surface of the culture vessel 15 may be irradiated with light emitted from the light source, and the position of the bottom surface may be detected based on the intensity of the reflected light. In addition, other known methods may be used.

In the present embodiment, the position of the bottom surface of the culture vessel 15 is set as the origin position. However, without being limited thereto, the position of the installation surface of a footing where cells are placed may be set as the origin position.

Then, the autofocus control unit 24 moves the focus position by a predetermined movement amount in a direction away from the position of the bottom surface of the culture vessel 15. Hereinafter, the direction away from the bottom surface of the culture vessel 15 is referred to as an upper direction, and a direction toward the bottom surface conversely is referred to as a lower direction.

Then, the number of nucleoli in a cell image captured when moving the focus position by a predetermined movement amount is counted, the focus position is moved upward by the movement amount corresponding to the counted number, and the number of nucleoli in a cell image captured at the focus position is counted. Then, again, the focus position is moved downward by the movement amount corresponding to the counted number, and the number of nucleoli in a cell image captured at the focus position is counted.

As shown in FIG. 4, in a case where the focus position is set at a position where a nucleolus is present, nucleoli appear most clearly in the cell image. Accordingly, the number of nucleoli is increased. On the other hand, in a case where the focus position is away from the position where a nucleolus is present, no nucleolus appears in the cell image. Accordingly, the number of nucleoli is reduced.

Therefore, as described above, by repeating the counting of the number of nucleoli in a cell image and the movement of the focus position by the movement amount corresponding to the counted number, a focus position where the number of nucleoli in a cell image is the largest is found as an optimal focus position.

It is assumed that the movement amount and the movement direction of the focus position corresponding to the number of nucleoli are set in advance. Specifically, as shown in FIG. 3, for example, the movement amount of the focus position may increase as the number of nucleoli decreases and the movement amount of the focus position may decrease as the number of nucleoli increases, and upward movement and downward movement may be alternately repeated by the number of times set in advance. In addition, a movable range to which the focus position can be moved from the origin position is set in advance, and the autofocus control unit 24 moves the focus position within the movable range.

In the present embodiment, autofocus control is performed based on the number of nucleoli in a cell image. However, the autofocus control may be performed based on the sum of the areas of individual nucleoli instead of the number of nucleoli. In this case, it is preferable to increase the movement amount of the focus position as the sum of the areas of individual nucleoli decreases and to decrease the movement amount of the focus position as the sum of the areas of individual nucleoli increases. Instead of nucleoli, the autofocus control may be performed based on the number of nuclei or the sum of the areas of nuclei or based on the number of cells or the sum of the areas of cells. In addition, the contrast of an image of nucleoli, nuclei, or cells may be calculated, and the autofocus control may be performed based on the contrast. In this case, it is preferable to increase the movement amount of the focus position as the contrast decreases and to decrease the movement amount of the focus position as contrast increases.

The movement amount and the movable range of the focus position may be changed according to information regarding the size of a cell or the size of a structure in a cell. A user may set and input the information regarding the size of a cell or a structure using the input device 5. As the information regarding the size of a cell or a structure, the size itself may be set and input, or the type of cell may be set and input. In addition, a table in which the information regarding the size of a cell or a structure is associated with the movement amount and the movable range may be set in advance for the autofocus control unit 24, and the movement amount and the movable range may be changed by referring to the table. For example, a table may be set so that the movement amount and the movable range increase as the size of a cell or a structure increases.

In addition, the movement amount or the movable range of the focus position may be changed according to culture conditions, such as a culture medium, a footing, and a seeding method, or a culture period from the seeding point in time.

Since the culture conditions are relevant to the cell growth rate, the movement amount or the movable range may be made to increase according to the culture conditions in which the cell growth rate increases. In addition, since the culture period is relevant to the growth of cells, the movement amount or the movable range may be made to increase as the culture period increases.

A user may set and input the culture conditions using the input device 5. A user may set and input the culture period, or a timer or the like may be provided to measure the culture period.

The input device 5 includes a mouse, a keyboard, and the like, and receives a setting input from the user. Specifically, the input device 5 receives a setting input of information regarding the size of a cell or a structure in a cell described above, culture conditions, and a culture period.

Figure 5:
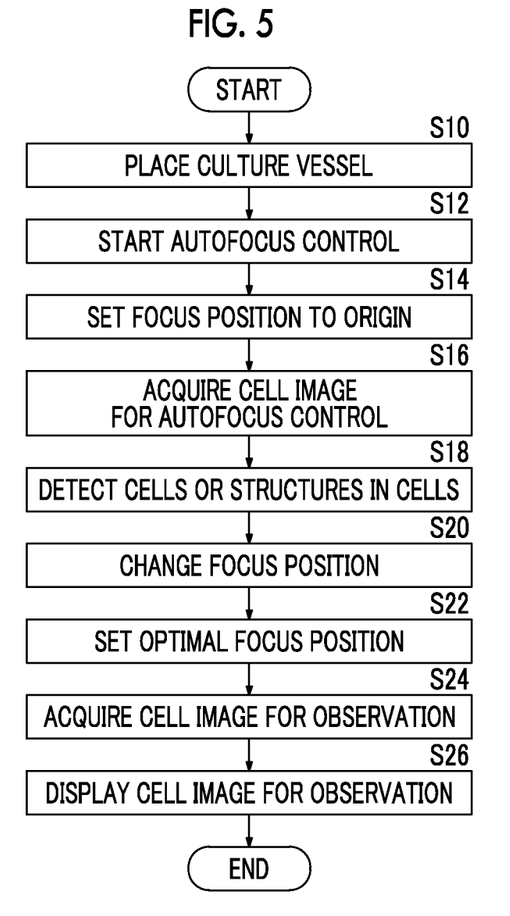
FIG. 5 is a flowchart illustrating the operation of the cell culture observation system using an embodiment of the cell imaging control device of the present invention.

Next, the operation of the above-described cell culture observation system will be described with reference to the flowchart shown in FIG. 5.

First, in the cell culture device 1, the transport unit 11 selects a culture to be imaged from a plurality of culture vessels housed therein, and places the selected culture vessel 15 on the stage 10 (S10).

Then, an autofocus control signal is output to the phase contrast microscope 3 from the autofocus control unit 24 of the cell imaging control device 2 (S12), and the phase contrast microscope 3 sets a focus position on the bottom surface of the culture vessel 15, which is the origin, by moving the phase difference lens 34 according to the input autofocus control signal (S14).

Then, the phase contrast microscope 3 sequentially captures a cell image for autofocus control while changing the focus position according to the autofocus control signal from the autofocus control unit 24, and outputs the cell image to the cell imaging control device 2.

The cell image for autofocus control output from the phase contrast microscope 3 is acquired by the cell image acquisition unit 21 of the cell imaging control device 2 (S16), and is output to the cell detection unit 22. The cell detection unit 22 detects cells or structures in cells from the input cell image, and outputs the information to the autofocus control unit 24 (S18).

As described above, for example, the autofocus control unit 24 counts the number of nucleoli, acquires the counted number as an autofocus evaluation value, and moves the focus position by outputting an autofocus control signal based on the autofocus evaluation value to the phase contrast microscope 3, thereby performing autofocus control (S20). Then, an optimal focus position is found and set (S22).

Then, the phase contrast microscope 3 captures a cell image for observation in a state in which the optimal focus position is set, and outputs the cell image for observation to the cell imaging control device 2. The cell image for observation output from the phase contrast microscope 3 is acquired by the cell image acquisition unit 21 (S24), and is output to the display control unit 25. The display control unit 25 displays the input cell image for observation on the display 4 (S26).

According to the cell culture observation system of the embodiment described above, a cell image is acquired by imaging transmitted light or reflected light of undyed cells, cells or structures in cells in the cell image are detected, an autofocus evaluation value is calculated based on the image information of the detected cells or structures, and an autofocus control signal based on the autofocus evaluation value is output to the imaging device. Therefore, it is possible to perform focus control with a focus on cells or structures in cells. For this reason, it is possible to capture a cell image, in which cells to be observed are in focus, without being influenced by floating matter, such as dead cells or dust, the height of cells themselves, and the like.

Figure 6:
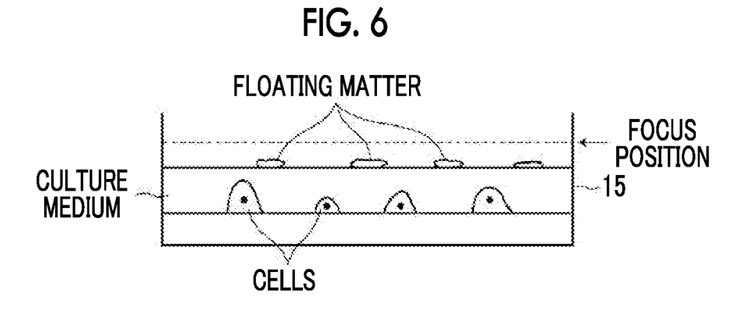
FIG. 6 is a diagram illustrating floating matter on a culture medium.

In the cell culture observation system of the embodiment described above, autofocus control is performed based on the image information of cells or structures detected by the cell detection unit 22. However, for example, as a result of moving the focus position, there is a case where the focus position is set above the surface of a culture medium (culture medium) as shown in FIG. 6.

In such a case, a more optimal focus position may be able to be set by performing the autofocus control again excluding the position of the surface of the culture medium rather than continuing the above autofocus control as it is.

Then, in the cell culture observation system of the embodiment described above, in a case where it is determined that there is a focus position where the floating matter described above is present, the focus position may be returned to the origin position, and autofocus control may be performed excluding the above-described focus position. Hereinafter, a cell culture observation system that performs such autofocus control will be described.

Figure 7:
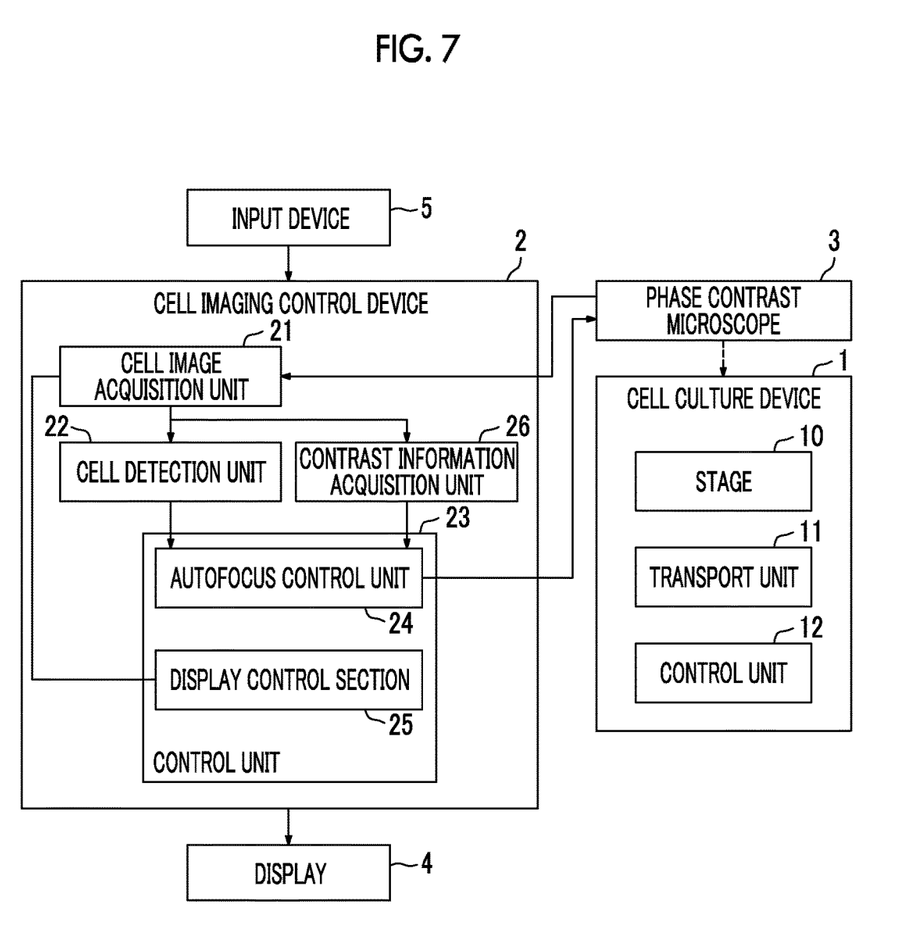
FIG. 7 is a diagram showing a modification example of the cell culture observation system shown in FIG. 1.

Specifically, as shown in FIG. 7, a contrast information acquisition unit 26 is further provided in the cell culture observation system of the embodiment described above. The contrast information acquisition unit 26 acquires the contrast information of the entire cell image acquired by the cell image acquisition unit 21. As the contrast information, for example, a difference between the maximum pixel value and the minimum pixel value in a cell image or a sum of differential values may be acquired by other known calculations.

Then, in a case where floating matter, such as dead cells or dust, is present as described above, the autofocus control unit 24 in the cell culture observation system shown in FIG. 7 performs the autofocus control again excluding the position of the surface of the culture medium where the floating matter is present.

Specifically, for a cell image captured at each focus position, the autofocus control unit 24 calculates an autofocus evaluation value based on the image information of cells or structures and an autofocus evaluation value based on the contrast information acquired by the contrast information acquisition unit 26.

Then, in a case where there is a focus position where the autofocus evaluation value based on the contrast information is the maximum and the autofocus evaluation value based on the image information of cells or structures is not the maximum, it is determined that there is a focus position where floating matter, such as dust or dead cells, is present, and a control signal to return the focus position to the origin position is output to the phase contrast microscope 3.

Then, the autofocus control unit 24 performs the autofocus control again. At this time, the focus control is limited to a range lower than the focus position where the autofocus evaluation value based on the contrast information is the maximum. Thus, it is possible to optimize the focus position with respect to living cells.

Next, the operation of the cell culture observation system shown in FIG. 7 will be described with reference to the flowchart shown in FIG. 8.

Figure 8:
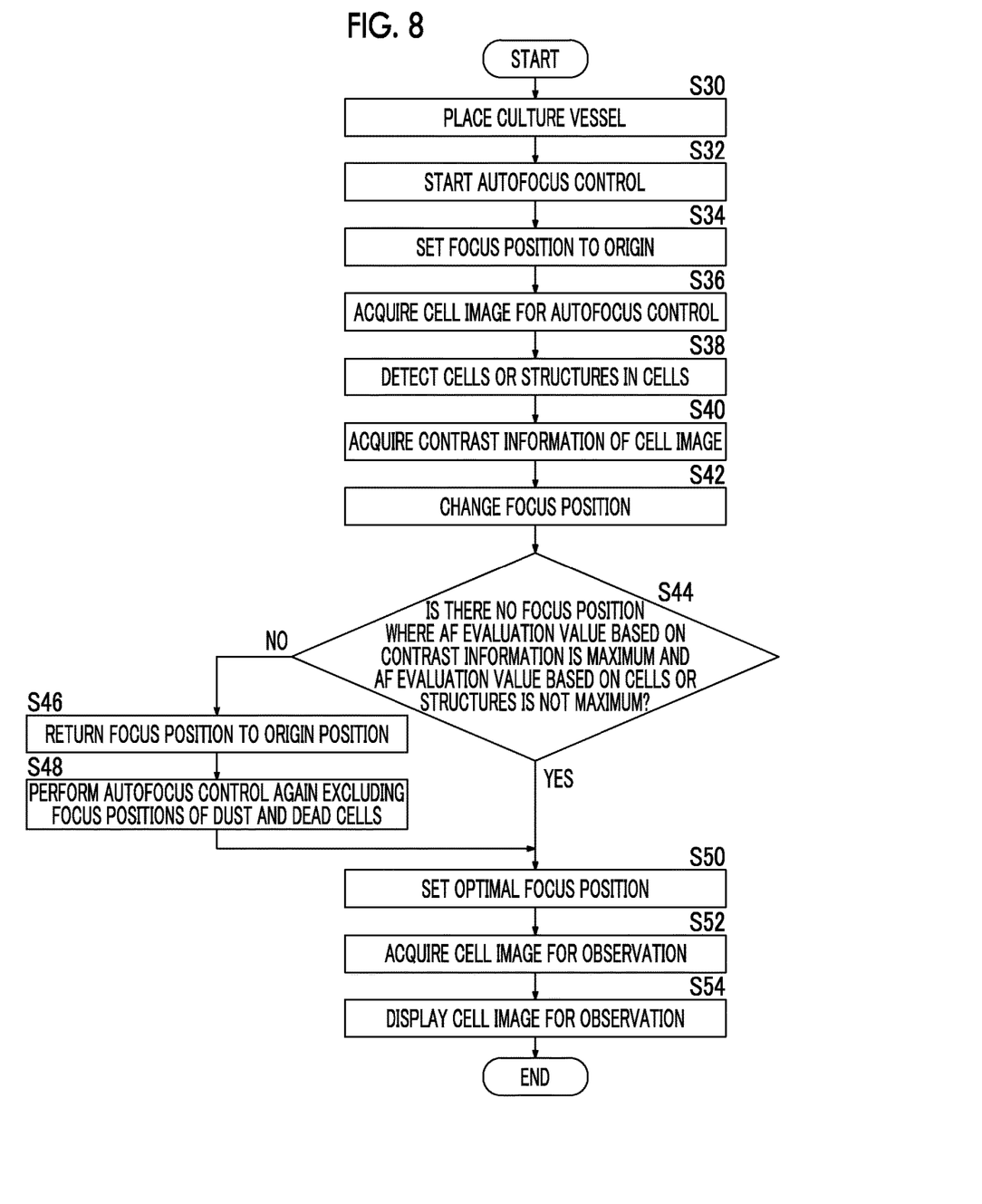
FIG. 8 is a flowchart illustrating the operation of the cell culture observation system shown in FIG. 7.

The operation up to the detection of cells or structures in cells in S30 to S38 shown in FIG. 8 is the same as that of the cell culture observation system of the embodiment described above. Then, the information of cells or structures in cells detected by the cell detection unit 22 is output to the autofocus control unit 24.

On the other hand, the cell image acquired by the cell image acquisition unit 21 is also output to the contrast information acquisition unit 26, and the contrast information acquisition unit 26 acquires the contrast information of the entire cell image that has been input (S40).

Then, as described above, for example, the autofocus control unit 24 acquires the number of nucleoli as an autofocus evaluation value, and moves the focus position by outputting an autofocus control signal based on the autofocus evaluation value to the phase contrast microscope 3 (S42), and acquires the contrast information of a cell image captured at each focus position.

The autofocus control unit 24 searches for a focus position where the autofocus evaluation value based on the number of nucleoli is the maximum and calculates an autofocus evaluation value based on the contrast information, and sequentially performs comparison between the autofocus evaluation value based on the contrast information and the autofocus evaluation value based on the number of nucleoli.

Then, the autofocus control unit 24 determines whether or not there is a focus position where the autofocus evaluation value based on the contrast information is the maximum and the autofocus evaluation value based on the number of nucleoli is not the maximum. In a case where it is determined that such a focus position is present, it is determined that there is a focus position where floating matter, such as dead cells or dust, is in focus (S44, NO).

In a case where it is determined that there is a focus position where floating matter, such as dead cells or dust, is in focus as described above, the autofocus control unit 24 outputs to the phase contrast microscope 3 a control signal to return the focus position to the origin position (S46).

Then, the autofocus control unit 24 excludes the focus position where floating matter, such as dead cells or dust, is in focus from the focus search range, and performs autofocus control again in a range on the origin position side of the focus position described above (S48), thereby finding and setting a focus position optimized for cells (S50).

Then, the phase contrast microscope 3 captures a cell image for observation in a state in which the optimal focus position is set, and outputs the cell image for observation to the cell imaging control device 2. The cell image for observation output from the phase contrast microscope 3 is acquired by the cell image acquisition unit 21 (S52), and is output to the display control unit 25. The display control unit 25 displays the input cell image for observation on the display 4 (S54).

In a case where it is determined that there is no focus position where the autofocus evaluation value based on the contrast information is the maximum and the autofocus evaluation value based on the number of nucleoli is not the maximum in S24 (YES), autofocus control using the autofocus evaluation value based on the number of nucleoli is continued as it is, and a focus position optimized for cells is found (S50).

According to the cell culture observation system shown in FIG. 7, an autofocus evaluation value based on the image information of cells or structures in cells and an autofocus evaluation value based on the contrast information are calculated, and a control signal to return the focus position to the origin position at the start of autofocus control is output to the imaging device in a case where there is a focus position where the autofocus evaluation value based on the contrast information is the maximum and the autofocus evaluation value based on the image information of cells or structures in cells is not the maximum. Therefore, it is possible to determine a focus position where the contrast is high due to dead cells or dust. In a case where such a focus position is present, it is possible to perform focus control again by returning the search position of the focus position to the origin position.

At this time, by performing autofocus control again in a range on the origin position side of the focus position where the autofocus evaluation value based on the contrast information described above is the maximum, it is possible to capture a cell image, in which a cell to be observed is in focus, without being influenced by floating matter, such as dead cells or dust.

In the embodiment described above, when the focus position is returned to the origin, the autofocus search range is automatically changed. Instead of this, the display control unit 25 may display, for example, a warning message indicating that floating matter, such as dead cells or dust, is present on the display 4, and the user may change the autofocus search range using the input device 5 by checking the message.

EXPLANATION OF REFERENCES

1: cell culture device
2: cell imaging control device
3: phase contrast microscope
4: display
5: input device
10: stage
11: transport unit
12: control unit
15: culture vessel
21: cell image acquisition unit
22: cell detection unit
23: control unit
24: autofocus control unit
25: display control unit
26: contrast information acquisition unit
33: objective lens
34: phase difference lens
35: objective lens
36: phase plate
37: imaging lens
38: imaging element

What is claimed is:

1. A cell imaging control device, comprising:
a cell detection unit that acquires a cell image by imaging transmitted light or reflected light of undyed cells by emission of light to the cells and detects the cells or structures in the cells in the cell image;
an autofocus control unit that calculates an autofocus evaluation value based on image information of the cells or the structures detected by the cell detection unit and outputs an autofocus control signal based on the autofocus evaluation value to an imaging device that captures the cell image; and
a contrast information acquisition unit that acquires contrast information of the cell image,
wherein the autofocus control unit calculates an autofocus evaluation value based on image information of the cells or the structures and an autofocus evaluation value based on the contrast information for the cell image captured by the imaging device using autofocus control based on the autofocus control signal, and outputs a control signal to return a focus position to an origin position at the start of autofocus control to the imaging device in a case where there is a focus position where the autofocus evaluation value based on the contrast information is a maximum and the autofocus evaluation value based on the image information of the cells or the structures is not a maximum.

2. The cell imaging control device according to claim 1, wherein, after returning the focus position to the origin position, the autofocus control unit performs the autofocus control in a range on the origin position side of a focus position where the autofocus evaluation value based on the contrast information is a maximum.

3. The cell imaging control device according to claim 1, wherein the origin position is a position of a bottom surface of a container on which the cells are cultured or a position of an installation surface on which the cells are placed.

4. The cell imaging control device according to claim 2, wherein the origin position is a position of a bottom surface of a container on which the cells are cultured or a position of an installation surface on which the cells are placed.

5. The cell imaging control device according to claim 1, wherein the autofocus control unit acquires the number of cells or structures or areas of the cells or the structures based on image information of the cells or the structures, and calculates the autofocus evaluation value based on the number or the areas.

6. The cell imaging control device according to claim 2, wherein the autofocus control unit acquires the number of cells or structures or areas of the cells or the structures based on image information of the cells or the structures, and calculates the autofocus evaluation value based on the number or the areas.

7. The cell imaging control device according to claim 1, wherein the autofocus control unit changes a movable range of a focus position.

8. The cell imaging control device according to claim 2, wherein the autofocus control unit changes a movable range of a focus position.

9. The cell imaging control device according to claim 7, wherein the autofocus control unit changes the movable range of the focus position based on information regarding sizes of the cells or the structures.

10. The cell imaging control device according to claim 8, wherein the autofocus control unit changes the movable range of the focus position based on information regarding sizes of the cells or the structures.

11. The cell imaging control device according to claim 1, wherein the structures are nucleoli or nuclei of the cells.

12. The cell observation device according to claim 1, wherein the cells are stem cells, cells sampled during efficacy testing, or cells sampled during biopsy.

13. A cell imaging control method using the cell imaging control device according to claim 1, comprising:
    acquiring a cell image by imaging transmitted light or reflected light of undyed cells by emission of light to the cells and detecting the cells or structures in the cells in the cell image; and
    calculating an auto focus evaluation value based on image information of the detected cells or structures and outputting an autofocus control signal based on the autofocus evaluation value to an imaging device that captures the cell image.

14. A non-transitory computer readable recording medium storing a cell imaging control program causing the cell imaging control device according to claim 1 as a computer to function as:
    a cell detection unit that acquires a cell image by imaging transmitted light or reflected light of undyed cells by emission of light to the cells and detects the cells or structures in the cells in the cell image; and
    an autofocus control unit that calculates an autofocus evaluation value based on image information of the cells or the structures detected by the cell detection unit and outputs an autofocus control signal based on the autofocus evaluation value to an imaging device that captures the cell image.

* * * * *